US007977272B2

(12) United States Patent
Miller et al.

(10) Patent No.: US 7,977,272 B2
(45) Date of Patent: Jul. 12, 2011

(54) PROCESS AND CATALYST FOR THE MANUFACTURE OF ACETIC ACID

(75) Inventors: Andrew John Miller, East Yorkshire (GB); George Ernest Morris, East Yorkshire (GB)

(73) Assignee: BP Chemicals Limited, Middlesex (GB)

( * ) Notice: Subject to any disclaimer, the term of this patent is extended or adjusted under 35 U.S.C. 154(b) by 754 days.

(21) Appl. No.: 11/793,237

(22) PCT Filed: Nov. 17, 2005

(86) PCT No.: PCT/GB2005/004438
§ 371 (c)(1),
(2), (4) Date: Mar. 18, 2008

(87) PCT Pub. No.: WO2006/064178
PCT Pub. Date: Jun. 22, 2006

(65) Prior Publication Data
US 2008/0269519 A1  Oct. 30, 2008

(30) Foreign Application Priority Data

Dec. 17, 2004 (GB) .................................. 0427821.4

(51) Int. Cl.
*B01J 27/185* (2006.01)
*B01J 27/053* (2006.01)
*B01J 27/13* (2006.01)
(52) U.S. Cl. .................... 502/213; 502/216; 502/230
(58) Field of Classification Search .................... None
See application file for complete search history.

(56) References Cited

U.S. PATENT DOCUMENTS

| 3,923,880 A | 12/1975 | Westlake et al. |
| 3,939,219 A | 2/1976 | Wilkinson |
| 4,664,851 A | 5/1987 | Drent |
| 6,127,432 A | 10/2000 | Wegman et al. |

FOREIGN PATENT DOCUMENTS

| GB | 1 326 014 | 8/1973 |
| GB | 2 123 404 A | 2/1984 |
| WO | WO 2005/009939 A1 | 2/2005 |
| WO | WO 2005/085162 A1 | 9/2005 |

OTHER PUBLICATIONS

White et al, Basic Energy Sciences Subcommittee Subpanel Workshop Report, Opportunities for Catalysis in the 21st Century, May 14-16, 2002, pp. 1-C5.*
Hjortkjaer, J., et al; "Rhodium ComplexCatalyzed Methanol Carbonylation. Effects of Medium and Various Additives"; *Industrial and Engineering Chemistry, Product Research and Development*, American Chemical Society; vol. 16, No. 4; pp. 281-285 (1977) XP000960422.
Smith, B.L., et al; "The Rhodium-Catalyzed Methanol Carbonylation to Acetic Acid at Low Water Concentrations: The Effect of Iodide and Acetate on Catalyst Activity and Stability"; *Journal of Molecular Catalysis*; vol. 39; pp. 115-136 (1987) XP000578542.

* cited by examiner

*Primary Examiner* — Paul A Zucker
(74) *Attorney, Agent, or Firm* — Nixon & Vanderhye

(57) ABSTRACT

Catalyst system for the production of acetic acid comprising a rhodium carbonylation catalyst, methyl iodide and at least one heteropolyacid promoter.

7 Claims, No Drawings

PROCESS AND CATALYST FOR THE MANUFACTURE OF ACETIC ACID

This application is the U.S. National Phase of International Application PCT/GB2005/004438, filed 17 Nov. 2005, which designated the U.S. PCT/GB2005/004438 claims priority to British Application No. 0427821.4, filed 17 Dec. 2004. The entire content of these applications are incorporated herein by reference.

The present invention relates to a process for the production of acetic acid and in particular, to a process for the production of acetic acid by carbonylation in the presence of a rhodium catalyst system.

The production of acetic acid by the carbonylation of methanol in the presence of a rhodium catalyst is known and is described, for example in, U.S. Pat. No. 3,769,329 and EP-A-0 161874

U.S. Pat. No. 3,769,329 describes a process for the production of carboxylic acids such as acetic acid by the reaction of an alcohol or the ester, ether and halide derivatives with carbon monoxide in the presence of a catalyst system comprising a rhodium component and a halogen component such as methyl iodide, hydrogen iodide, iodine or the like.

U.S. Pat. No. 5,227,519 describes a process for the production of carboxylic acids by the carbonylation of an alcohol in a liquid reaction medium containing a rhodium catalyst, an allyl iodide, an iodide salt and a trihaloacetic acid promoter.

EP-A-0161874 describes a process for the production of a carboxylic acid wherein an alcohol such as methanol is reacted with carbon monoxide in a liquid reaction medium containing a rhodium catalyst stabilized with an iodide salt such as lithium iodide along with an allyl iodide and an alkyl acetate and a finite concentration of water.

It has now been surprisingly found that by using certain non-hydrohalogenoic acids in a rhodium-catalysed carbonylation process for the production of acetic acid improved carbonylation rates may be achieved.

Thus, according to the present invention there is provided a catalyst system for the production of acetic acid which catalyst system comprises a rhodium carbonylation catalyst, methyl iodide, and at least one non-hydrohalogenoic acid promoter in the substantial absence of alkali metal iodides, alkaline earth iodides, metal complexes capable of generating $I^-$, and salts capable of generating $I^-$.

The present invention also provides a process for the production of acetic acid by reacting carbon monoxide with methanol and/or a reactive derivative thereof in the substantial absence of alkali metal iodides, alkaline earth iodides, metal complexes capable of generating $I^-$, salts capable of generating $I^-$ in a liquid reaction composition comprising methyl acetate, a finite concentration of water, acetic acid and a catalyst system comprising a rhodium carbonylation catalyst, methyl iodide and at least one non-hydrohalogenoic acid promoter.

The present invention further provides for the use of a catalyst system for the production of acetic acid which catalyst system comprises a rhodium carbonylation catalyst, methyl iodide, and at least one non-hydrohalogenoic acid promoter in the substantial absence of alkali metal iodides, alkaline earth iodides, metal complexes capable of generating $I^-$, salts capable of generating $I^-$.

The non-hydrohalogenoic acid for use in the process present invention may suitably be at least one of an oxoacid, a superacid and a heteropolyacid. Mixtures of non-hydrohalogenoic acids of the same or different type may be used such as mixtures of at least two different oxoacids or at least two different superacids or at least two different heteropolyacids or a mixture of at least one oxoacid and/or at least one superacid and/or at least one heteropolyacid. It will be understood by the skilled person that an acid may be both of the oxoacid and a superacid type.

Oxoacids are compounds with X—OH groups of the type $H_nXO_m$ wherein X is a non-metal or metal and n and m are integers. Examples of common oxoacids are $H_3PO_4$, $H_2SO_4$, $HNO_3$ and $HClO_4$ Suitable oxoacids for use in the process of the present invention include the oxoacids of the elements of Groups 13 to 17 of the Periodic Table.

Suitable oxoacids of the elements of Group 13 include the oxoacids of boron such as $H_3BO_3$. Group 14 oxoacids include those of germanium such as $H_4GeO_4$. Group 15 oxoacids include the oxoacids of nitrogen, phosphorus and arsenic. Suitable nitrogen-containing oxoacids include $HNO_3$ and $HNO_2$. Examples of phosphorus-containing oxoacids include $H_3PO_4$, $H_3PO_3$ and $H_3PO_2$. Examples of arsenic-containing oxoacids include $H_3AsO_3$. Group 16 oxoacids include the oxoacids of sulphur such as $H_2SO_4$, $H_2SO_3$, triflic acid, p-toluenesulphonic acid, selenium, for example $H_2SeO_3$ and $H_2SeO_4$ and tellurium such as $H_6TeO_6$. Group 17 oxoacids may be oxoacids of bromine, iodine and chlorine such as HBrO, HClO, $H_5IO_6$, $HClO_2$ and $HClO_4$.

Preferred oxoacids are $H_2SO_4$, $HNO_3$ and $H_3PO_4$ or mixtures thereof.

Acidity can be measured in a wide variety of solvents. Typically the acidity of a substance is measured in water and the hydrogen ion concentration generated by the substance therein is often given in terms of the pH scale. Solutions of a substance having a pH lower than 7.0 are acidic; those of higher pH are alkaline. However, the concepts of hydrogen ion concentration and pH are meaningful only for dilute aqueous solutions of acids. Thus, a widely used means for determining acidity in other media and at high concentrations is the Hammett acidity function $H_0$. The acidity function, $H_0$, is defined as $$H_0 = pK_{BH+} - \log [BH^+]/[B]$$

where [B] is concentration of a weak base (indicator)
[$H^+$] is concentration of the conjugate acid of the weak base
$pK_{BH+}$ is pK of indicator in water The $H_0$ value of an acidic substance is measured using indicators that are weak bases (B) such as o-nitroaniline or 2,4-dinitroaniline. The weak base is (partly) converted in the acidic substance to the conjugate acid of the base ($BH^+$). The value of $[BH^+]/[B]$ is typically measured by spectrophotometric means. By using the known pK in water for the base, $H_0$ can then be calculated for the acidic substance.

Acidic substances with $-H_0$ values above about 12 are referred to as superacids. Superacids are upward of $10^6$ times as strong as a 1 molar aqueous solution of a strong acid. Acids with a $-H_0$ of greater than 12.1 (measured as the pure acid), are suitable for use in the process of the present invention.

The superacids for use in the process of the present invention have non-coordinating anions by which is meant that little or no covalent interaction between the anion and iridium.

Suitable superacids for use in the process of the present invention include acids which have the following anions $BF_4^-$, $PF_6^-$, $(CF_3SO_2)_2N^-$, $CBH_6Br_6^-$, $CF_3SO_3^-$, $SbF_6^-$, $FSO_3^-$ or mixtures thereof.

Specific examples of suitable superacids include $HBF_4$, $HPF_6$, $(CF_3SO_2)_2NH$ and $HCBH_6Br_6$.

Heteropolyacids are well known. The term "heteropolyacid" as used herein and throughout the specification means the free acid and/or the associated metal salts thereof. Typically, the heteropolyacid anion comprises from two to eighteen oxygen-linked polyvalent metal atoms, which are generally known as the "peripheral" atoms. These peripheral atoms surround one or more central atoms in a symmetrical manner. The peripheral atoms are usually one or more of molybdenum, tungsten, vanadium, chromium, niobium, tantalum and other metals. The central atoms are usually silicon or phosphorus but can comprise any one of a large variety of atoms from Groups I-VIII in the Periodic Table of elements. These include, for instance, cupric ions; divalent beryllium, zinc, cobalt or nickel ions; trivalent boron, aluminium, gallium, iron, cerium, arsenic, antimony, phosphorus, bismuth, chromium or rhodium ions; tetravalent silicon, germanium, tin, titanium, zirconium, vanadium, sulphur, tellurium, manganese nickel, platinum, thorium, hafnium, cerium ions and other rare earth ions; pentavalent phosphorus, arsenic, vanadium, antimony ions; hexavalent tellurium ions; and heptavalent iodine ions. Such heteropolyacids are also known as "polyoxoanions", "polyoxometallates" or "metal oxide clusters". The structures of some of the well known anions are named after the original researchers in this field such as the structures known as Keggin, Wells-Dawson and Anderson-Evans-Perloff structures.

Heteropolyacids may be represented by the formula $H_3M_{12}XO_{40}$ where M is tungsten, molybdenum, chromium, vanadium, tantalum or niobium and X is phosphorous or silicon.

Preferably, the heteropolyacid is selected from silicotungstic acids, silicomolybdic acids, phosphotungstic acids, phosphomolybdic acids such as the following acids:

| | |
|---|---|
| 12-tungstophosphoric acid | $H_3[PW_{12}O_{40}] \cdot xH_2O$ |
| 12-molybdophosphoric acid | $H_3[PMo_{12}O_{40}] \cdot xH_2O$ |
| 12-tungstosilicic acid | $H_4[SiW_{12}O_{40}] \cdot xH_2O$ |
| 12-molybdosilicic acid | $H_4[SiMo_{12}O_{40}] \cdot xH_2O$ |

Heteropolyacids usually have a high molecular weight, for example, in the range from 700-8500 and include dimeric complexes. They have a relatively high solubility in polar solvents such as water or other oxygenated solvents, especially if they are free acids.

The non-hydrohalogenoic acid for use in the process of the present invention may be introduced directly into the reactor, together with or separately from a reactant feed stream. The non-hydrohalogenoic acid may be used in the form of an aqueous solution of the acid.

The amount of the non-hydrohalogenoic acid to be used in the process of the present invention should be sufficient to provide a promotional effect on the carbonylation rate. The exact amount will depend on the specific non-hydrohalogenoic used and, in particular, on the nature and concentration of the anion of the acid. Without wishing to be bound by any theory, it is believed that certain anions, such as those of oxoacids, may co-ordinate to the rhodium metal, and thus, if the concentration of these oxoanions is too high, a detrimental effect of the carbonylation rate may ensue. However, if the anion is non-coordinating to the rhodium metal, higher concentrations of the acid may be employed.

Suitably, the amount of a superacid which may be added to the liquid reaction composition is such that the molar ratio of the anion to rhodium is in the range [greater than 0 to 2.5]:1, preferably, in the range [greater than 0 to 1]:1, especially, in the range [0.05 to 0.5]:1.

Typically, the amount of oxoacid which may be added to the liquid reaction composition is such that the molar ratio of anion to rhodium is in the range [greater than 0 to 0.4]:1. Where the anion is $SO_4^{2-}$, $NO_3^-$ or $PO_4^{3-}$, derived from sulphuric, nitric and phosphoric acids respectively; the molar ratio of anion to rhodium is preferably in the range [greater than 0 to 0.4]:1, suitably [greater than 0 to 0.35]:1, such as in the range [0.05 to 0.3]:1.

Suitably, the amount of a heteropolyacid which may be added to the liquid reaction composition is such that the molar ratio of the anion to rhodium is in the range [greater than 0 to 15]:1, preferably, in the range [greater than 4 to 12]:1, especially, in the range [8 to 11]:1.

The rhodium catalyst in the liquid reaction composition may comprise any rhodium containing compound which is soluble in the liquid reaction composition. The rhodium catalyst may be added to the liquid reaction composition in any suitable form which dissolves in the liquid reaction composition or is convertible to a soluble form. Examples of suitable rhodium-containing compounds which may be added to the liquid reaction composition include $[Rh(CO)_2Cl]_2$, $[Rh(CO)_2I]_2$, $[Rh(Cod)Cl]_2$, rhodium (III) chloride, rhodium (III) chloridetrihydrate, rhodium (III) bromide, rhodium (III) iodide, rhodium (III) acetate and rhodium dicarbonylacetylacetonate.

Preferably, the rhodium catalyst concentration in the liquid reaction composition is in the range 50 to 5000 ppm by weight of rhodium, preferably 100 to 1500 ppm.

Where the non-hydrohalogenoic acid is a superacid and/or a heteropolyacid, there may be optionally employed in the liquid reaction composition a co-promoter selected from alkali metal iodides, alkaline earth metal iodides, metal complexes capable of generating $I^-$, salts capable of generating $I^-$, and mixtures of two or more thereof.

Accordingly, the present invention provides a catalyst system for the production of acetic acid which catalyst system comprises a rhodium carbonylation catalyst, methyl iodide, at least one non-hydrohalogenoic acid promoter selected from a superacid, a heteropolyacid and mixtures thereof and optionally a co-promoter selected from alkali metal iodides, alkaline earth iodides, metal complexes capable of generating $I^-$, and salts capable of generating $I^-$ and mixtures thereof.

The present invention also provides a process for the production of acetic acid by reacting carbon monoxide with methanol and/or a reactive derivative thereof in a liquid reaction composition comprising methyl acetate, a finite concentration of water, acetic acid and a catalyst system comprising a rhodium carbonylation catalyst, methyl iodide and at least one non-hydrohalogenoic acid promoter selected from a superacid, a heteropolyacid and mixtures thereof and optionally a co-promoter selected from alkali metal iodides, alkaline earth iodides, metal complexes capable of generating $I^-$, salts capable of generating $I^-$ and mixtures thereof.

Suitable alkali metal iodides include lithium iodide. Suitable alkaline earth metal iodides include calcium iodide. Suitable metal complexes capable of generating $I^-$ include complexes of the lanthanide metals, for example, lanthanum and cerium, and nickel, iron, aluminium and chromium, typically $Al(OAc)_2(OH)$ and $Ce(OAc)_3$. hydrate. Salts capable of generating $I^-$ include, for example, acetates which are capable of conversion in-situ to $I^-$ and organic salts, such as quaternary ammonium iodides and phosphonium iodides, which may be added as such. A preferred co-promoter is lithium iodide.

The co-promoter selected from alkali metal iodides, alkaline earth metal iodides, metal complexes capable of generating $I^-$, salts capable of generating $I^-$, and mixtures of two or more thereof is suitably added to the liquid reaction composition in an amount such that the amount of ionic iodide ($I^-$) generated is in the range 5 to 20 wt %.

In the process of the present invention, the concentration of methyl iodide co-catalyst in the liquid reaction composition is preferably in the range 5 to 16% by weight.

In the process of the present invention, suitable reactive derivatives of methanol include methyl acetate, dimethyl ether and methyl iodide. A mixture of methanol and reactive derivatives thereof may be used as reactants in the process of the present invention. Water is required as co-reactant for ether or ester reactants. Preferably, methanol and/or methyl acetate are used as reactants.

At least some of the methanol and/or reactive derivative thereof will be converted to, and hence present as, methyl acetate in the liquid reaction composition by reaction with the carboxylic acid product or solvent. Preferably, the concentration of methyl acetate in the liquid reaction composition is in the range 0.5 to 40% by weight, more preferably 0.5 to 30% by weight.

Water may be formed in-situ in the liquid reaction composition, for example, by the esterification reaction between methanol reactant and acetic acid product Small amounts of water may also be produced by hydrogenation of methanol to produce methane and water. Water may be introduced to the carbonylation reactor together with or separately from other components of the liquid reaction composition. Water may be separated from other components of reaction composition withdrawn from the reactor and may be recycled in controlled amounts to maintain the required concentration of water in the liquid reaction composition. The water concentration in the liquid reaction composition is suitably in the range 1-20 wt %, such as 1-10 wt %, such as in the range 2-10 wt %.

The carbon monoxide reactant may be essentially pure or may contain inert impurities such as carbon dioxide, methane, nitrogen, noble gases, water and $C_1$ to $C_4$ paraffinic hydrocarbons. The presence of hydrogen in the carbon monoxide feed and generated in-situ by the water gas shift reaction is preferably kept low as its presence may result in the formation of hydrogenation products. Thus, the amount of hydrogen in the carbon monoxide reactant is preferably less than 1 mol %, more preferably less than 0.5 mol % and yet more preferably less than 0.3 mol % and/or the partial pressure of hydrogen in the carbonylation reactor is preferably less than $1 \times 10^5$ N/m$^2$ partial pressure, more preferably less than $5 \times 10^4$ N/m$^2$ and yet more preferably less than $3 \times 10^4$ N/m$^2$. The partial pressure of carbon monoxide in the reactor is suitably in the range $1 \times 10^5$ N/m$^2$ to $7 \times 10^6$ N/m$^2$, preferably $1 \times 10^5$ N/m$^2$ to $3.5 \times 10^6$ N/m$^2$, more preferably $1 \times 10^5$ N/m$^2$ to $1.5 \times 10^6$ N/m$^2$.

The total pressure of the carbonylation reaction is suitably in the range $1 \times 10^6$ N/m$^2$ to $2 \times 10^7$ N/m$^2$, preferably $1.5 \times 10^6$ N/m$^2$ to $1 \times 10^7$ N/m$^2$, more preferably $1.5 \times 10^6$ N/m$^2$ to $5 \times 10^6$ N/m$^2$.

The temperature of the carbonylation reaction is suitably in the range 100 to 300° C., preferably in the range 150 to 220° C.

The process of the present invention may be performed as a batch or as a continuous process, but is preferably performed as a continuous process.

The acetic acid product may be recovered from the liquid reaction composition by withdrawing vapour and/or liquid from the carbonylation reactor and recovering acetic acid from the withdrawn material. Preferably, acetic acid is recovered from the liquid reaction composition by continuously withdrawing liquid reaction composition from the carbonylation reactor and recovering acetic acid from the withdrawn liquid reaction composition by one or more flash and/or fractional distillation stages in which the acetic acid is separated from the other components of the liquid reaction composition such as rhodium catalyst, methyl iodide, methyl acetate, unreacted methanol, water and acetic acid solvent which may be recycled to the reactor to maintain their concentrations in the liquid reaction composition.

The invention will now be illustrated by way of example only and with reference to the following examples:

General Reaction Method

All experiments were performed in a 300 cm$^3$ zirconium autoclave equipped with a stirrer, liquid injection facility, ballast vessel and gas feed lines. The gas and liquid feed inlet valves were opened and the assembly pressure tested with nitrogen (minimum 30 barg). The nitrogen was vented from the unit and followed by flushing with carbon monoxide (3×3 barg cycles). The autoclave was opened to vent. Specified amounts of methyl iodide followed by water, acetic acid and methyl acetate were added via a funnel before the autoclave was resealed. Specified amounts of rhodium, non-hydrohalogenoic acid, acetic acid and lithium iodide (when used) were placed into the catalyst injector. The autoclave stirrer was switched on (1500 rpm) before pressurising with carbon monoxide. The assembly was heated to reaction temperature (190° C.). The temperature in the autoclave was kept constant by controlling the flow of cooling water. The reaction was monitored until the gas uptake had ceased. On completion of the run the autoclave was cooled to below 30° C. The autoclave was then vented. The major component in each batch carbonylation was acetic acid.

The rate of gas uptake at a certain point in a reaction run was used to calculate the carbonylation rate, as number of moles of reactant consumed per liter of cold degassed reactor composition per hour (mol·dm$^{-3}$·hr$^{-1}$) at a particular reactor composition (total reactor composition based on a cold degassed volume).

Methyl acetate concentration was calculated during the course of the reaction from the starting composition, assuming that one mole of methyl acetate was consumed from every mole of carbon monoxide that was consumed. No allowance was made for the organic components in the autoclave headspace.

EXAMPLES

TABLE 1

| Example | HeteroPolyAcid (HPA) | Rh/HPA anion Molar Ratio | Methyl Acetate (g) | Acetic Acid (g) | Water (g) | MeI (g) | HPA (g) | Rh[a] (g) | LiI (g) |
|---|---|---|---|---|---|---|---|---|---|
| A | None | 1:0 | 30 | 70 | 27 | 23.7 | 0 | 0.15 | 0 |
| 1 | $H_3[PW_{12}O_{40}]$·xH$_2$O | 1:9 | 30 | 52 | 27 | 23.6 | 17.5 | 0.15 | 0 |
| B | None | 1:0 | 30 | 89 | 8 | 23.6 | 0 | 0.15 | 0 |
| 2 | $H_3[PW_{12}O_{40}]$·xH$_2$O | 1:9 | 30 | 71 | 8 | 23.6 | 17.5 | 0.15 | 0 |
| C | None | 1:0 | 30 | 71 | 8 | 23.6 | 0 | 0.15 | 16.3 |
| 3 | $H_3[PW_{12}O_{40}]$·xH$_2$O | 1:9 | 30 | 55 | 8 | 23.6 | 17.5 | 0.15 | 16.3 |

[a]Rh added as [RhCl(CO)$_2$]$_2$

TABLE 2

| Example | Rate at 12% MeOAc (moLdm$^{-3}$·hr$^{-1}$) |
|---|---|
| A | 11.2 |
| 1 | 17.8 |
| B | 6.4 |
| 2 | 17.7 |
| C | 12.3 |
| 3 | 18.3 |

As can be seen from a comparison of Examples A and B (not according to the invention) and Examples 1 and 2 a significant increase in the carbonylation rate can be achieved in the presence of a heteropolyacid. In addition, an increase in rate can also be achieved by the addition of a heteropolyacid to a lithium iodide promoted rhodium catalyst.

The invention claimed is:

1. A catalyst system for the production of acetic acid comprising a rhodium carbonylation catalyst, methyl iodide and at least one heteropolyacid promoter.

2. A catalyst according to claim 1 which is in the absence of alkali metal iodides, alkaline earth metal iodides, metal complexes capable of generating I$^-$ and salts capable of generating I$^-$.

3. A catalyst according to claim 1 which further comprises a copromoter selected from alkali metal iodides, alkaline earth metal iodides, metal complexes capable of generating I$^-$, salts capable of generating I$^-$ and mixtures thereof.

4. A catalyst according to claim 3 wherein the co-promoter is selected from lithium iodide, calcium iodide, quaternary ammonium iodides, phosphonium iodides and complexes of the lanthanide metals, nickel, iron, aluminium and chromium.

5. A catalyst according to claim 4 wherein the co-promoter is lithium iodide.

6. A catalyst according to claim 1, 2, 3, 4 or 5 wherein the heteropolyacid is selected from silicotungstic acids, silicomolybdic acids, phosphotungstic acids, phosphomolybdic acids and mixtures thereof.

7. A catalyst according to claim 6 wherein the heteropolyacid is selected from 12-tungstophosphoric acid, 12-molybdophosphoric acid, 12-tungstosilicic acid, 12-molybdosilicic acid and mixtures thereof.

* * * * *